United States Patent [19]

Riemann

[11] Patent Number: 5,407,243

[45] Date of Patent: Apr. 18, 1995

[54] TICK REMOVING DEVICE

[76] Inventor: Mathew W. Riemann, 4909 Yates Mill Pond Rd., Raleigh, N.C. 27606

[21] Appl. No.: 165,078

[22] Filed: Dec. 10, 1993

[51] Int. Cl.$^6$ ............................................. A01M 3/00
[52] U.S. Cl. ........................................ 294/100; 606/210
[58] Field of Search .............. 294/99.2, 100; 606/206, 606/210

[56] References Cited

U.S. PATENT DOCUMENTS

| | | | |
|---|---|---|---|
| 216,918 | 6/1879 | Wales | 606/210 X |
| 284,118 | 8/1883 | Cilley | 606/210 X |
| 987,173 | 3/1911 | Salé | 294/100 |
| 1,141,742 | 6/1915 | Wiseman | 294/100 X |
| 2,752,625 | 7/1956 | Ponsell | 294/100 X |
| 3,481,641 | 12/1969 | Berger et al. | 294/100 |
| 3,844,291 | 10/1974 | Moen | 294/100 X |
| 4,442,837 | 4/1984 | Keatley | 294/99.2 X |
| 4,979,771 | 12/1990 | Childs, III | 294/99.2 |
| 5,002,323 | 3/1991 | Idsund | 294/100 |

FOREIGN PATENT DOCUMENTS

| | | | |
|---|---|---|---|
| 891959 | 3/1944 | France | 294/99.2 |
| 339051 | 7/1921 | Germany | 606/210 |
| 93009917 | 5/1993 | WIPO | 294/100 |

*Primary Examiner*—Dean J. Kramer
*Attorney, Agent, or Firm*—Rhodes, Coats & Bennett

[57] ABSTRACT

A tick removing device for removing a tick embedded in a human or animal host. In the preferred embodiment, the tick removing device includes an elongated sleeve with a gripping device inserted therethrough. The gripping device includes a pair of flexible and spaced apart legs that are movable between open and closed positions. An actuator button is disposed in the rear end of the sleeve and secured to the gripping device for moving the gripping device between the open and closed positions. A spring is disposed in the elongated sleeve for biasing the actuator button and attached gripping device toward a closed position. The gripping device is moved to an open position by depressing the actuator button which moves the attached gripping device in a forward direction through the sleeve. A pin mounted in the sleeve extends between the gripping legs and is sized to wedge the gripping legs apart as the gripping device moves through the sleeve. The user positions the gripping legs about an attached tick while in an open position and releases the actuator button to close the gripping legs and grip the tick. With the tick gripped, the tick removing device is rotated two to three revolutions to cause the tick to release its grip on the host.

4 Claims, 3 Drawing Sheets

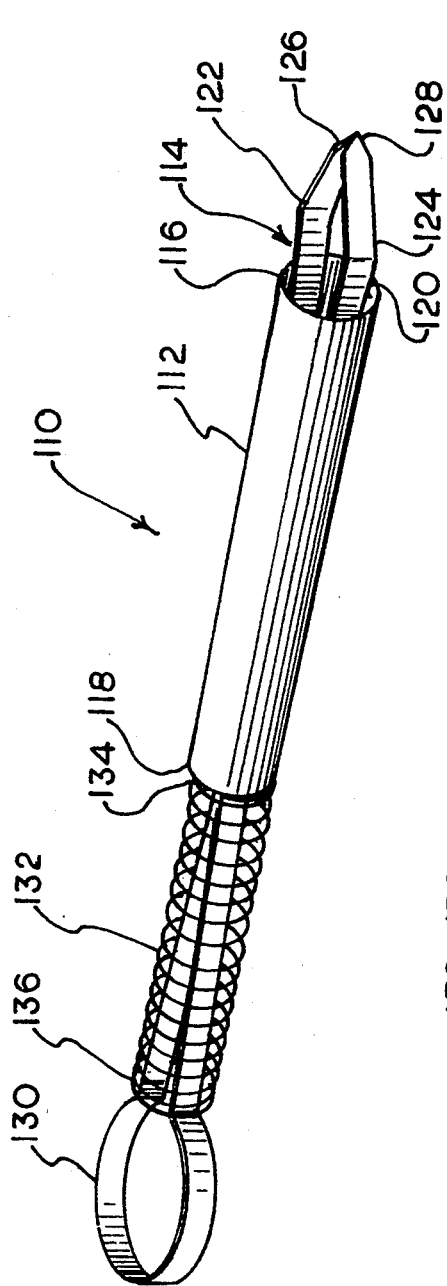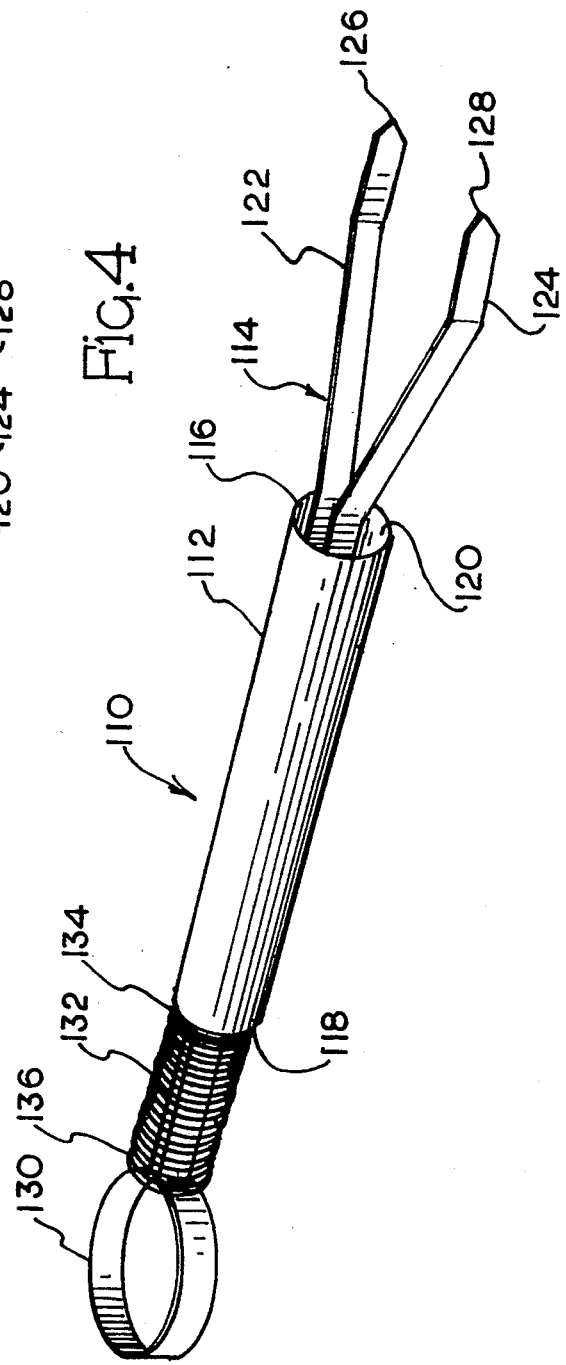

TICK REMOVING DEVICE

FIELD OF THE INVENTION

This invention relates to a method and apparatus for removing ticks from people, pets and other animals.

BACKGROUND OF THE INVENTION

Ticks can transmit a number of diseases such as Rocky Mount Spotted Fever and Lyme Disease to people and animal hosts. Thus, a tick should be quickly and effectively removed from the host. Improperly removing a tick from a host can increase the chance of the tick infecting the host with a disease or causing other medical problems.

Ticks are often difficult to remove from the host because they insert a portion of their mouth part into the host to reach the blood supply and also secrete an adherent cement onto the skin of the host to help anchor themselves to the host. If a tick is removed improperly from the host, the tick can be mutilated and the head of the tick torn off and left embedded in the host. Such an improper removal of a tick increases the chance that the tick will infect the host with a disease and that the area on the host where a portion of the tick's head is left embedded will become infected.

Prior art tick removing devices and methods that attempt to effectively remove an attached tick are known. Prior art tick removing devices are disclosed in U.S. Pat. Nos. 4,303,268; 4,442,837; 4,976,718; 4,979,771; 5,002,323; 5,078,729; 5,116,347; and 5,137,318.

In order for a tick removing device to be capable of removing a tick effectively, the tick removing device must be capable of securely gripping the tick during the tick removal process. Prior art tick removing devices often require that the user continuously squeeze or apply a pressure to the tick-removing device during the tick removal process. The removal of a tick is more difficult if the user must continuously apply a pressure to the tick removing device in order to grip the tick. In particular, if the person or animal moves while the tick is being removed, the user may loose his or her grip on the tick removing device causing the tick to slip from the tick removing device.

Prior art tick removing devices also often have relatively complex designs, and accordingly are difficult to manufacture and are expensive. Tick removing devices also often tend to wear out after repeated use so that they fail to sufficiently grip a tick to allow for the tick's effective removal.

SUMMARY AND OBJECTS OF THE INVENTION

The tick removing device of the present invention overcomes the above discussed problems of prior art tick removing devices. In a preferred embodiment of the invention, the tick removing device includes a gripping device disposed within an elongated sleeve. The gripping device includes a pair of spaced-apart and opposed gripping legs with attached gripping points. The gripping legs can be opened and closed to grip a tick with the gripping points.

An actuator button is disposed in a rear end of the sleeve and is secured to the gripping device for opening and closing the gripping device. The gripping device is biased toward the closed position by a spring disposed in the sleeve and engaged with the actuator button. To position the tick removing device in the open position, the actuator button is depressed to overcome the bias of the spring such that the gripping device is moved forward through the sleeve. A pin is mounted in the sleeve and extends between the gripping legs so that the gripping legs are wedged apart by the pin as the gripping device is moved forwardly through the sleeve.

To remove a tick attached to a host, the actuator button is depressed and held to position the tick removing device in an open position. The gripping points are then positioned about the tick and the actuator button released such that the gripping points close about and grip the tick. The gripping points remain in their closed position about the tick because the tick removing device is biased toward the closed position. Accordingly, the gripping legs and gripping points are constructed to remain in the closed position during the tick removal process. Once the tick is gripped, the tick removing device is rotated counterclockwise two to three revolutions to loosen the tick's grip on the host so that the tick can be safely removed from the host.

Accordingly, it is an object of the present invention to provide a tick removing device that is inexpensive and relatively simple.

Another object of the present invention is to provide a tick removing device that is normally biased toward a closed position.

Another object of the present invention is to provide a tick removing device that is durable.

Another object of the present invention is to provide a tick removing device that is easy to handle and operate. dr Other objects and advantages of the present invention will become apparent and obvious from a study of the following description and the accompanying drawings which are merely illustrative of such invention.

BRIEF DESCRIPTION OF THE DRAWINGS

FIG. 4 is a perspective view of a second design of the tick removing device with the same being disposed in the closed position.

FIG. 5 is a perspective view of a second design of the tick removing device with the same being disposed in the open position.

DETAILED DESCRIPTION OF THE INVENTION

Figure 1:
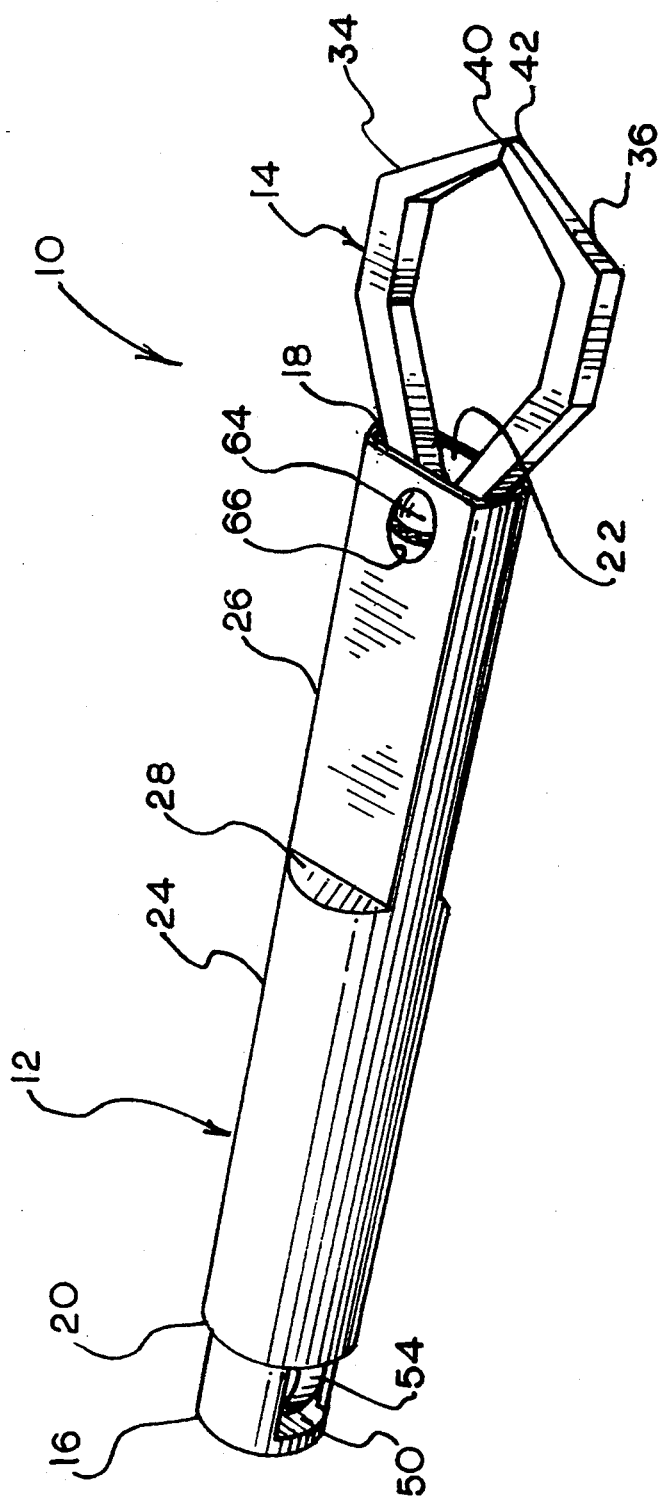
FIG. 1 is a perspective view of a first design for the tick removing device of the present invention.

With further reference to the drawings, one embodiment of the present invention tick removing device is indicated generally by the numeral 10. Tick removing device 10 is used to grip and remove a tick that has become attached to a person, pet, or other host. Tick removing device 10 generally includes a sleeve 12 having a gripping device 14 extending therethrough. The gripping device 14 is connected to an actuator button 16 which is used to position gripping device 14 between open and closed positions for selectively gripping a tick.

Sleeve 12 is an elongated cylinder made from plastic or other suitable material and includes a front end 18 and a rear end 20. Extending from front end 18 to rear end 20 is a channel 22. Sleeve 12 has a rear section 24 and an integral front section 26 with the diameter of the rear section 24 being greater than the diameter of the front section 26. The differences in the diameters of the rear and front sections 24 and 26 result in a shoulder 28 being formed at the junction of the rear and front sections 24 and 26. The shoulder 28 provides a finger support for a user gripping the tick removing device 10.

Extending through sleeve 12 is gripping device 14. Gripping device 14 is preferably made from a nylon-type plastic and includes spaced apart and opposed gripping legs 34 and 36 that define a slot 38 extending therebetween. At one end of gripping legs 34 and 36 are a pair of opposed gripping points 40 and 42 and at the opposite end is an elongated rear section 44. Gripping legs 34 and 36 and gripping points 40 and 42 are movable between an open position shown in FIG. 2 and a closed position shown in FIG. 3.

Elongated rear section 44 is connected to actuator button 16 for opening and closing gripping device 14. The actuator button 16 is constructed from plastic or other suitable material and has a cylindrical shape with a channel 48 extending therethrough. Actuator button 16 is sized to fit within the rear end 20 of sleeve 12. A pair of opposed openings 50 and 52 lead into channel 48 and mate with projections 54 and 56 formed on the elongated rear section 44 of gripping device 14. Projections 54 and 56 extend through openings 50 and 52 and secure actuator button 16 and gripping device 14 together. Projections 54 and 56 may be designed with a slot 57 extending therebetween so that they can be depressed together and removed from openings 50 and 52 in order to detach actuator button 16 from gripping device 14.

Figure 3:
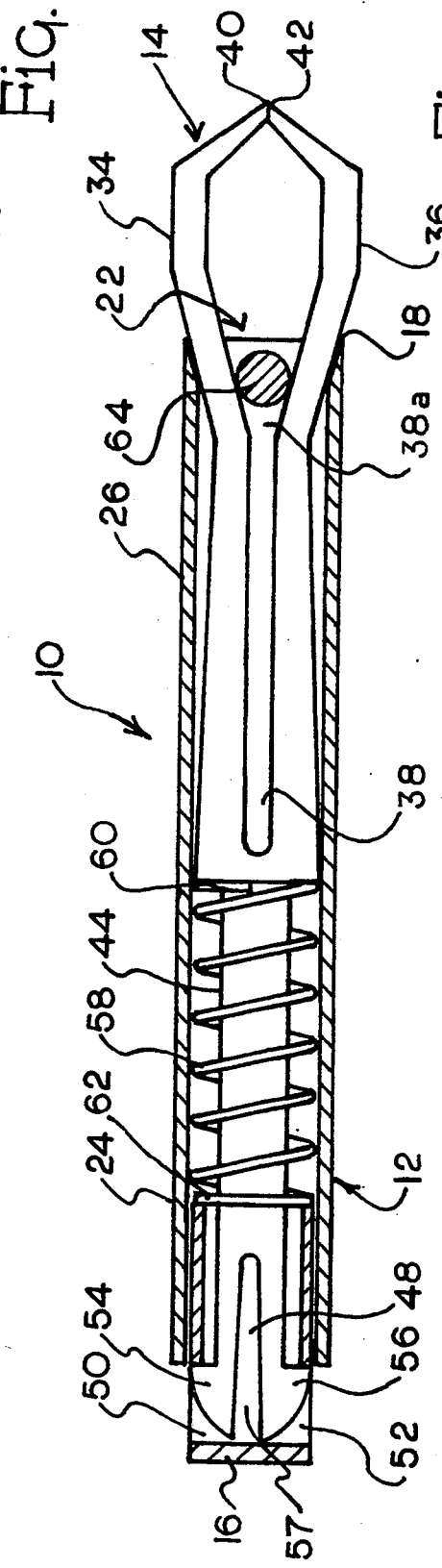
FIG. 3 is a side sectional view of the tick removing device shown in FIG. 1 with the device being shown in the closed position.

Actuator button 16 enables a user to position gripping device 14 longitudinally within sleeve 12. A spring 58 is disposed within the rear section 24 of sleeve 12 and around elongated rear section 44 of gripping device 14. Spring 58 biases actuator button 16 and attached gripping device 14 in a rearward direction such that gripping device 14 is retracted and the closed gripping points 40 and 42 extend just outside front end 18 of sleeve 12. A front end 60 of spring 58 engages shoulder 28 within sleeve 12, while a rear end 62 of spring 58 engages actuator button 16 so as to bias gripping device 14 in a rearward direction. As shown in FIG. 3, gripping device 14 assumes a normally biased closed position.

To open gripping device 14, actuator button 16 is depressed such that the bias of spring 58 is overcome and the gripping device 14 is moved forwardly to an extended position. Mounted within the front end 18 of sleeve 12 is a pin 64. Pin 64 is mounted through a pin opening 66 extending through sleeve 12 and extends transversely through channel 22 such that it is disposed between gripping legs 34 and 36. Pin 64 is disposed in a rearwardly tapering section 38a of the slot 38 defined by gripping legs 34 and 36. Pin 64 is sized with respect to the tapering section 38a of slot 38 such that the gripping legs 34 and 36 are wedged apart into an open position as the gripping device 14 is moved forwardly through sleeve 12 by actuator button 16.

Figure 2:
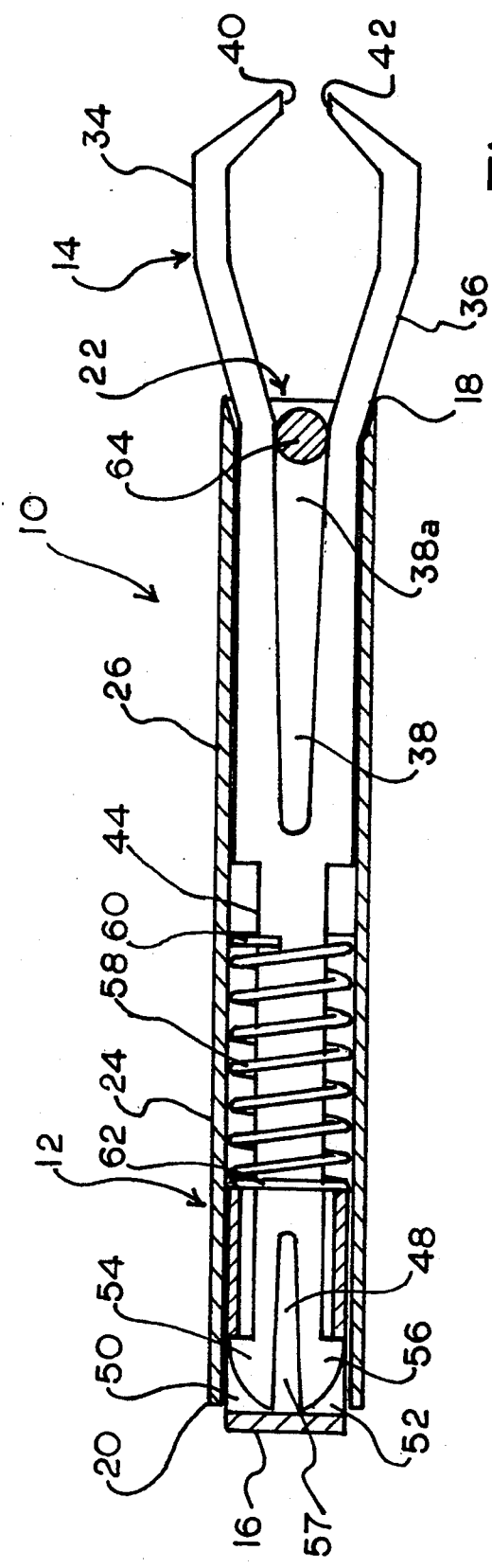
FIG. 2 is a side sectional view of the tick removing device shown in FIG. 1 with the device being shown in the open position.

In operation, the embodiment of tick removing device 10 shown in FIGS. 1–3 is used as follows. The user grips tick removing device 10 in one hand by positioning sleeve 12 between the index and middle fingers such that the index and middle fingers rest on shoulder 28. Gripping points 40 and 42 of gripping device 14 are then disposed adjacent an attached tick. As shown in FIG. 3, the gripping points 40 and 42 are initially biased in a closed position.

The user depresses actuator button 16 with his or her thumb in a forward direction to open gripping legs 34 and 36 and the attached gripping points 40 and 42. Actuator button 16 is forwardly pressed with sufficient force to overcome the spring bias and compress spring 58. As actuator button 16 moves forward the attached gripping device 14 likewise moves forwardly through sleeve 12. Pin 64 mounted in sleeve 12 and positioned between gripping legs 34 and 36 is sized so that as gripping device 14 moves forwardly gripping legs 34 and 36 are wedged apart by pin 64. The user must maintain pressure on the actuator button 16 to maintain gripping legs 34 and 36 in the open position.

The user then positions the open gripping points 40 and 42 of the gripping device 14 around the attached tick. In particular, the gripping points 40 and 42 are positioned to grip the body portion of the tick located at the surface of the host. With the gripping device 14 positioned around the embedded tick, the user slowly releases actuator button 16. Spring 58 forces actuator button 16 and attached gripping device 14 rearwardly through sleeve 12 as actuator button 16 is released. As gripping device 14 moves rearwardly, gripping legs 34 and 36 move to the closed position and gripping points 40 and 42 come together and grip the attached tick. Spring 58 maintains the gripping device 14 in the closed position so that the tick is continuously gripped by the gripping device 14.

Once the tick is gripped, the tick removing device 10 is rotated two to three counterclockwise revolutions. During the revolution of the tick removing device 10, the gripping device 14 is maintained in the closed position by spring 58. Accordingly, the attached tick cannot become inadvertently detached from gripping device 14. Rotating tick removing device 10 causes the attached tick to detach from the host without the head of the tick remaining embedded under the skin. The detached tick gripped by gripping device 14 is then disposed of by depressing actuator button 16 to position the gripping device in an open position where the tick is released at a disposal site.

Referring to FIGS. 4–5, an alternate embodiment tick removing device 110 is shown therein. Tick removing device 110 includes a sleeve 112 and a gripping device 114 extending therethrough.

Sleeve 112 includes an elongated cylindrical shape and is preferably made of stainless steel. A channel 120 extends from a front end 116 to a rear end 118.

Gripping device 114 is made of stainless steel spring sheet metal and includes a pair of opposed gripping legs 122 and 124. Gripping legs 122 and 124 have opposed gripping points 126 and 128 at one end and are attached together with a circular head 130 at the opposite end. The gripping legs 122 and 124 and attached gripping points 126 and 128 are biased to normally assume a spaced-apart, open position. Gripping legs 122 and 124 extend through sleeve 112 and are pressed together by sleeve 112. Circular head 130 extends from the rear end 118 of sleeve 112, while the gripping points 126 and 128 extend from the front end 116 of sleeve 112.

Located around gripping device 114 between circular head 130 and the rear end 118 of sleeve 112 is a spring 132. Spring 132 has a front end 134 positioned adjacent the rear end 118 of sleeve 112 and a rear end 136 positioned adjacent the head 130 of gripping device 114. Spring 132 biases gripping device 114 in a rearward direction to position gripping device 114 in a closed position as shown in FIG. 4. Tick removing device 110 is positionable in an open position by sliding sleeve 112 in a rearward direction to compress spring 132 and extend gripping legs 122 and 124 through the front end 116 of sleeve 112. As the gripping legs 122 and 124 move through sleeve 112, the gripping points 128 and 130 open as shown in FIG. 5.

In operation, tick removing device 110 operates as follows. One grips sleeve 112 between the index and middle finger of one hand with the thumb resting on the head 130 of gripping device 114. As shown in FIG. 4, tick removing device 110 is initially in a closed position with gripping points 126 and 128 positioned together. The user opens tick removing device 110 by depressing the head 130 of the gripping device 114 with his or her thumb such that gripping device 114 moves forwardly through sleeve 112. Gripping points 128 and 130 open as sleeve 112 is retracted and gripping legs 122 and 124 move past the front end 116 of sleeve 112.

With the tick removing device 110 in the open position, the user positions gripping points 126 and 128 about the tick. Head 130 of the gripping device 114 is gradually released to place tick removing device 110 in a closed position. As head 130 of the gripping device is released, spring 132 forces gripping device 114 in a rearward direction and sleeve 112 in an opposite forward direction. The front end 116 of sleeve 112 is sized so that gripping points 126 and 128 are pressed together as the gripping legs 122 and 124 are retracted into sleeve 112.

The gripping points 126 and 128 are positioned by the user to close about the body section of the tick close to the skin of the host. Spring 132 biases tick removing device 110 in the closed position to help ensure that tick removing device 110 does not become detached from the tick during the tick removing process. Once the tick has become gripped by the tick removing device 110, the user rotates the tick removing device 110 two to three counterclockwise revolutions. Rotating the tick removing device 110 causes the tick to become detached from the host. Removal of the tick in this manner helps prevent the head of the tick from being detached and remaining embedded in the host. Upon removal of the tick, the tick removing device is opened to release the tick at a disposal site.

The tick removing devices 10 and 110 of the present invention provide a safe and effective tool for removing ticks. The tick removing devices 10 and 110 are both biased in a closed position to help prevent the tick from being inadvertently detached during the removal process. The tick removing devices 10 and 110 are also designed to be practical, inexpensive and durable.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A tick removing device comprising:
a) an elongated open sleeve having a tick removing end and an actuating end;
b) a gripping device disposed in the elongated open sleeve and movable back and forth therein, the gripping device including a main body portion disposed within the sleeve and extending out the tick removing end of the sleeve, and a connecting body portion disposed interiorly within the sleeve;
c) the main body portion of the gripping device including an elongated slot that extends from an intermediate portion of the sleeve down the main body portion of the gripping device and out the tick removing end of the sleeve, the slot defining two spaced apart main body portions that are disposed interiorly of the elongated open sleeve and wherein the spaced apart main body portions form a pair of spaced apart gripping legs that extend out from the tick removing end of the sleeve and wherein the exposed gripping legs include a pair of spaced apart tick gripping points and wherein the gripping legs are movable between opened and closed positions and wherein in the closed position the gripping legs disposed exterior of the sleeve bulge outwardly to the extent that the gripping legs may not be fully retracted within the sleeve and thusly limit the movement of the gripping device within the sleeve towards the actuating end of the sleeve;
d) the connecting portion of the gripping device extending from the main body portion through the elongated sleeve towards the actuating end of the sleeve, the connecting body portion including a slotted terminal end that includes at least one locking projection formed thereon, and wherein the connecting body portion is smaller in diameter than the elongated sleeve and defines a spring cavity outwardly of the connecting body portion but within the elongated sleeve;
e) a detachably connected actuator button disposed within the actuating end of the sleeve and movable back and forth therein, the actuating button including a hollow sleeve having an outer wall structure that moves within the elongated sleeve about the actuating end of the sleeve and wherein there is provided at least one opening formed within the wall of the hollow sleeve that forms the actuator button;
f) the actuator button being engaged with and detachably coupled to the connecting body portion of the gripping device as the slotted terminal end of the connecting body portion is inserted within the actuator button and wherein the locking projection formed on the slotted terminal end of the connecting body projects outwardly through the opening formed in the wall of the sleeve that forms the actuator button so as to securely couple and lock the actuator button with the connecting body portion of the gripping device, and wherein the actuator button includes a spring stop portion that is formed about an internal end of the actuator button;
g) a shoulder formed internally within the elongated sleeve between the main body portion of the gripping device and the actuator button and which functions as a spring stop;
h) a spring disposed within the elongated sleeve and surrounding the connecting body portion of the gripping device and wherein the spring is engaged on one end with the actuator button and on the other end with the shoulder such that the spring tends to bias the gripping device for movement towards the actuating end of the sleeve which consequently result in the biasing tending to withdraw the gripping legs of the main body portion into the sleeve; and i) a fixed spreader pin secured within the sleeve and extending transversely across the sleeve and particularly disposed within the slot formed between the spaced apart main body portions of the main body such that as the actuator button is pressed and pushed toward the tick removing end of the sleeve the fixed spreader pin causes the gripping legs of the main body to spread and move toward an open position and wherein the release of the actuator button results in the spring moving the actuator button through the actuating end of the sleeve causing the main body of the gripping device to be moved towards the actuating end of the sleeve and which results in the sleeve itself, about the tick removing end, constricting the gripping legs and causing the gripping legs to be moved towards a closed position as the main body is retracted and moved towards the actuating end of the sleeve.

2. The tick removing device of claim 1 wherein the slot formed in the main body portion of the gripping device becomes progressively narrow towards the connecting body portion of the gripping device.

3. The tick removing device of claim 1 wherein the diameter of the tick removing end of the sleeve is smaller than the diameter of the actuating end of the sleeve and wherein there is formed an exterior shoulder sized for a user to grip as the actuator button is depressed and wherein the formed exterior shoulder forms a transition between the smaller and larger diameter portions of the sleeve.

4. The tick removing device of claim 1 wherein the slotted terminal end of the connecting portion of the gripping device includes a pair of locking projections that project outwardly therefrom and wherein the wall of the actuator button includes a pair of spaced apart openings formed therein for receiving the pair of locking projections formed on the slotted terminal end of the connecting portion of the gripping device, whereby the connecting portion of the gripping device can be easily and quickly attached and detached from the actuator button by compressing the slotted terminal end of the connecting portion so as to move the pair of locking projections with respect to the spaced apart openings formed in the wall of the actuator button.

* * * * *